United States Patent
Gualtieri et al.

(10) Patent No.: US 9,340,375 B2
(45) Date of Patent: May 17, 2016

(54) METHOD AND APPARATUS FOR DISCONTINUOUS APPLICATIONS, AT A CONSTANT PITCH, OF CONTROLLED QUANTITIES OF ABSORBENT MATERIAL IN GRANULES

(71) Applicants: Diego Gualtieri, Sulmona (IT); Albert Prous, Pescara (IT)

(72) Inventors: Diego Gualtieri, Sulmona (IT); Albert Prous, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 0 days.

(21) Appl. No.: 14/204,005

(22) Filed: Mar. 11, 2014

(65) Prior Publication Data

US 2014/0270994 A1    Sep. 18, 2014

(30) Foreign Application Priority Data

Mar. 12, 2013 (IT) ............... TO2013A0195

(51) Int. Cl.
*B65G 53/44* (2006.01)
*A61F 13/15* (2006.01)

(52) U.S. Cl.
CPC .......... *B65G 53/44* (2013.01); *A61F 13/15617* (2013.01); *A61F 13/15658* (2013.01)

(58) Field of Classification Search
CPC ............................... B05B 12/04; B65G 53/44
USPC ......... 222/410, 373, 362, 363, 335, 199–200, 222/409, 251; 118/314; 241/84.3
See application file for complete search history.

(56) References Cited

U.S. PATENT DOCUMENTS

| 535,260 | A | * | 3/1895 | McPherson | ............ | B65G 65/44 |
| | | | | | | 222/199 |
| 2,037,694 | A | * | 4/1936 | Broun | ..................... | G01F 11/24 |
| | | | | | | 222/339 |

(Continued)

FOREIGN PATENT DOCUMENTS

| EP | 1 974 705 A1 | 10/2008 |
| EP | 2 286 776 A1 | 2/2011 |
| IT | TO2013A000195 | * 3/2013 |

OTHER PUBLICATIONS

Mar. 12, 2013 Search Report for Italian Patent Application No. TO2013A000195 (7 pages).

*Primary Examiner* — Kevin P Shaver
*Assistant Examiner* — Robert Nichols, II
(74) *Attorney, Agent, or Firm* — Popovich, Wiles & O'Connell, P.A.

(57) ABSTRACT

A device (20) suitable for transforming a continuous and controlled flow (320) of absorbent material in granules (310) into an intermittent flow (250) for providing to receiving means (50, 60) movable along a direction X, comprising a feed manifold (210), an outlet nozzle (500) and a main body (200), placed between said feed manifold (210) and said outlet nozzle (500), configured to cause said absorbent material in granules (310) to flow along a direction (Y'-Y') coinciding with the respective axes of symmetry of said feed manifold (210), said outlet nozzle (500) and said main body (200); wherein within said main body (200) a movable element (240) is housed, capable of moving alternately between a first and a second working position, in such a way that when said movable element (240) is located in the first working position, it forms a first accumulation chamber (230) of the absorbent material in granules (310) fed in a continuous manner (320), and a first discharge duct (233) of said material (310), and when said movable element is in the second working position, it forms a second accumulation chamber (251) and a second discharge duct (253).

3 Claims, 6 Drawing Sheets

(56) References Cited

U.S. PATENT DOCUMENTS

| | | | | |
|---|---|---|---|---|
| 2,620,946 A | * | 12/1952 | Auer | B65G 65/44 222/310 |
| 2,779,512 A | * | 1/1957 | Steele | B65D 83/06 222/307 |
| 2,814,261 A | * | 11/1957 | Meagher | A21C 15/002 222/281 |
| 3,353,723 A | * | 11/1967 | Wieleba | D21C 7/06 222/368 |
| 3,584,765 A | * | 6/1971 | Orr, Jr. | G01N 1/04 193/2 B |
| 4,053,087 A | * | 10/1977 | Lack | G01F 11/24 222/278 |
| 5,279,854 A | | 1/1994 | Kendall et al. | |
| 5,975,374 A | | 11/1999 | Vargas et al. | |
| 6,627,241 B1 | * | 9/2003 | DeMars | A21C 11/163 118/25 |
| 2003/0224704 A1 | * | 12/2003 | Shank | B24C 7/0092 451/38 |
| 2013/0025792 A1 | | 1/2013 | Ninomiya et al. | |

* cited by examiner

METHOD AND APPARATUS FOR DISCONTINUOUS APPLICATIONS, AT A CONSTANT PITCH, OF CONTROLLED QUANTITIES OF ABSORBENT MATERIAL IN GRANULES

TECHNICAL FIELD

The present description relates to an apparatus and the relative method suitable for discontinuous applications, at a constant pitch, of controlled quantities of material, for example absorbent material in granules on a moving substrate, designed to be advantageously used, for example, as an absorbent structure in disposable sanitary hygiene products such as pant-type wearable diapers, in all their possible configurations and uses, or rather, both in the open configuration and in the closed configuration, better known as "training pants" or "pull-ons", both for child and adult use.

TECHNOLOGICAL BACKGROUND

In the field of disposable sanitary hygiene articles at the end of the 1980s, absorbent material in granules was introduced for forming their absorbent structure, which was previously composed of just cellulose fibers.

The absorbent material in granules that is normally used in this type of disposable hygiene products is composed of super-absorbent polymers capable of absorbing and retaining large quantities of liquids.

Super Absorbent Polymers (SAP) can, in turn, have granules of different sizes and shapes, according to the different production methods.

The production of an absorbent structure can be carried out in several ways. One of the most common methods is carried out by depositing and/or mixing the absorbent polymers granules on a strip composed of synthetic and/or natural fibers that can be absorbent, for example cellulose fibers.

The desire of all manufacturers of disposable sanitary hygiene products is to be able to concentrate the absorbent material in areas where it is most used, i.e. to create discontinuous applications of the absorbent polymer granules, always maintaining control of the weight and the geometric parameters of the application, such as the length and width of the applied dose and pitch of application between the various doses; so as to achieve a higher quality product that, at the same time, results in a saving in terms of cost, and creates products with a lower environmental impact as they are made with a smaller quantity of materials.

Systems are known in the art that are able to apply a quantity of absorbent polymer material in granules in a discontinuous manner suitable for producing absorbent structures for disposable sanitary articles. According to the known, well described embodiments, for example, in patent document EP 1 621 165 A1, such systems consist of a rotary dispensing cylinder provided, on its outer surface, with a plurality of slots and/or recesses arranged at the deposition area, and having dimensions that ensure the deposition of the correct quantity of absorbent material in granules or SAP. The rotary dispensing cylinder is normally placed at the bottom of a reservoir from which it picks up the material in granules. Subsequently, by rotating, the cylinder carries the slots and/or recesses, filled with SAP, into a second area or discharge area where it releases it. The discharge area is normally diametrically opposite to the loading area, and the material discharged from the dispensing cylinder can be deposited on a moving strip.

The inventors have observed that apparatus such as the one described above have numerous limitations and/or problems such as, for example, the control of the quantity of the absorbent material in granules applied to each product, which can be done only in an indirect manner.

Indeed, the weight of material introduced in the production method of the absorbent structure can only be determined with the aid of the apparent density of the material in granules, in other words, the quantity of SAP that is required for depositing on the absorbent products is defined solely by the volume of the slots and/or the recesses present on the outer surface of the dispensing roller, which are intended to be filled by said absorbent polymeric material in granules.

It should be recalled that the density or volumic mass of a body is defined as the ratio between the mass of a body and its volume.

The definition of density provided above refers to a quantity of solid and homogeneous matter, i.e. without internal voids. This value is also known as the real or absolute density, since it only takes into account the volume of the solid fraction.

For solid materials with closed cavities, with open cavities or spongy structures, or for granular matter contained in the recipients, such as sand, grains or as in our case absorbent material in granules, the concept of apparent density of a body is introduced, which is calculated in a manner formally analogous to the absolute density, but takes into account the total volume occupied by the solid, thus its external dimensions, including the empty spaces present inside.

This type of control has very important limitations related, specifically, to the variability of the apparent density. Indeed, the apparent density changes according to the pressure head variation in granular material present in the loading reservoir, the variation in the environmental conditions (temperature, humidity) and not least to the variation in size of the granules themselves, which of course can vary between one supplier and another, but also to the variation in production batches from the same supplier.

Furthermore, the slots and/or recesses have difficulty filling and emptying their contents with increasing velocities of the production machines. To overcome this difficulty, dispensing cylinders are provided with gripping and releasing means of the absorbent material in granules. To do this, the bottom of the slots and/or recesses of the dispensing cylinder are rendered permeable to air, and connected to a source of sub-atmospheric pressure during the loading phase, and subsequently, to a high pressure pneumatic source during the phase of expulsion or discharge.

This system, while solving the problem of filling and emptying of the dispensing roller in high-velocity production lines, in turn, generates new problems such as, for example, increasing the complexity and consequently the cost of the dispensing roller and the increase in maintenance operation costs due to the need to always keep the air-permeable area of the slots and recesses clean.

In addition to what has already been said, the problem linked to the change in production size, and therefore the specifications, of the absorbent structure, must not be forgotten. Indeed, it is evident that each format of the absorbent structure is also characterized, in addition to its dimensions, by the quantity and distribution of the absorbent material in granules. Therefore, each of the said formats of the absorbent structure requires its own specific dispensing roller, which, obviously, must be replaced when the size of the product to be produced changes.

OBJECT AND SUMMARY

The object of the present invention is to provide instructions for producing a device capable of carrying out the applications of discrete quantities of material in granules, for example, of shape- and weight-controlled absorbent polymers, on a moving receiving means, for example, a continuous sheet, designed, for example, to be advantageously used as an absorbent structure in disposable sanitary hygiene products.

According to the invention, this object is achieved thanks to an application device having the characteristics referred to specifically in the claims that follow.

The invention also relates to a corresponding production method.

The claims form an integral part of the technical disclosure herein provided in relation to the invention.

BRIEF DESCRIPTION OF THE DRAWINGS

The invention will now be described, purely by way of non-limiting example, with reference to the attached drawings, wherein.

DETAILED DESCRIPTION OF EMBODIMENTS

In the following description, various specific details are illustrated aimed at a thorough understanding of the embodiments. The embodiments can be implemented without one or more of the specific details, or with other methods, components, materials, etc.

In other cases, known structures, materials or operations are not illustrated or described in detail to avoid obscuring the various aspects of the embodiments The reference to "an embodiment" in the context of this description indicates that a particular configuration, structure or feature, described in relation to the embodiment, is included in at least one embodiment. Therefore, phrases such as "in an embodiment", possibly present in different places of this description do not necessarily refer to the same embodiment.

Furthermore, particular conformations, structures, or features can be combined in any suitable manner in one or more embodiments.

Figure 1:
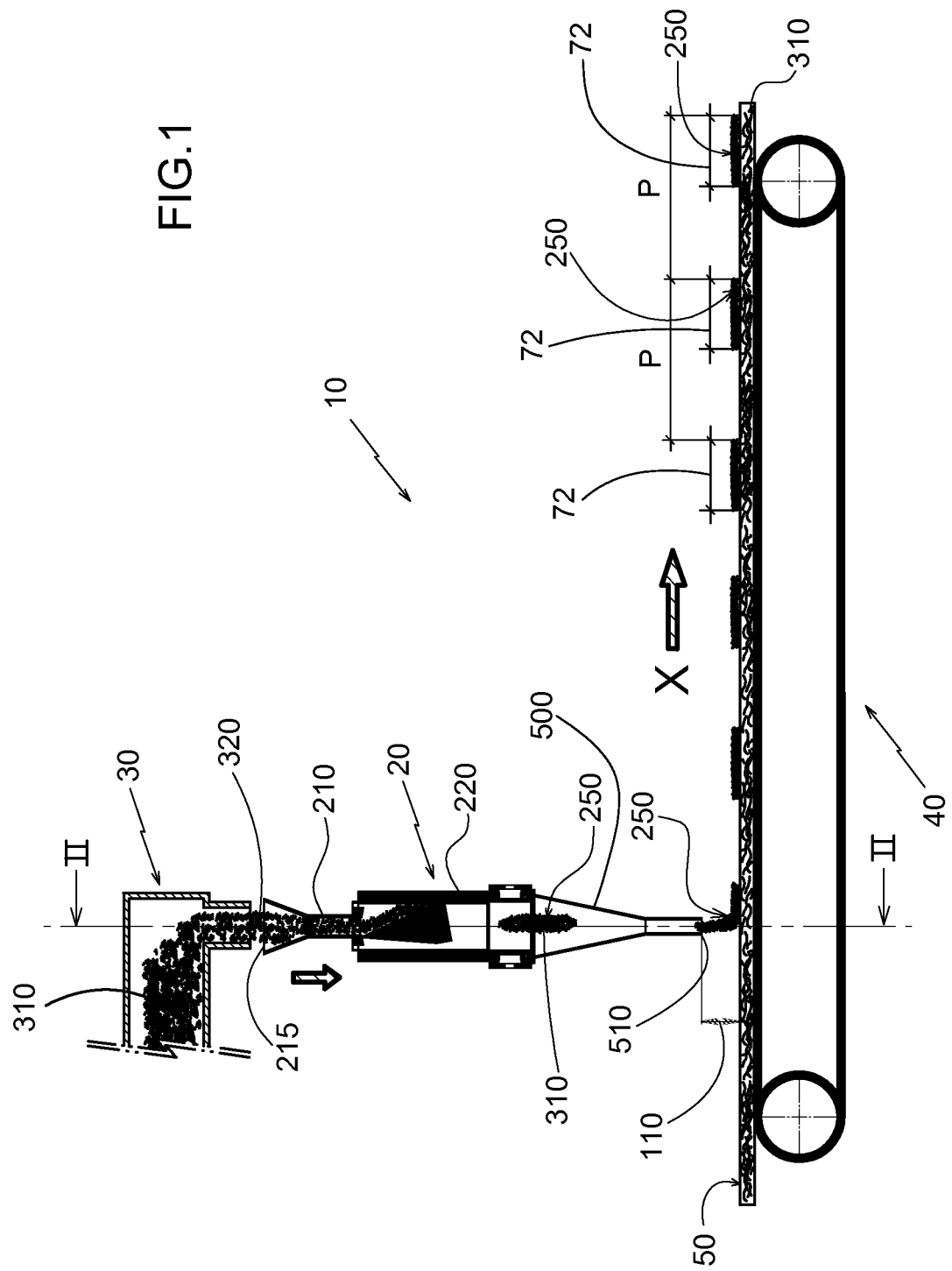
FIGS. 1 and 6 are, respectively, the schematic view of two types of production methods for the construction of absorbent structures, which use the equipment, subject of the present invention, of FIG. 2.
Figure 2:
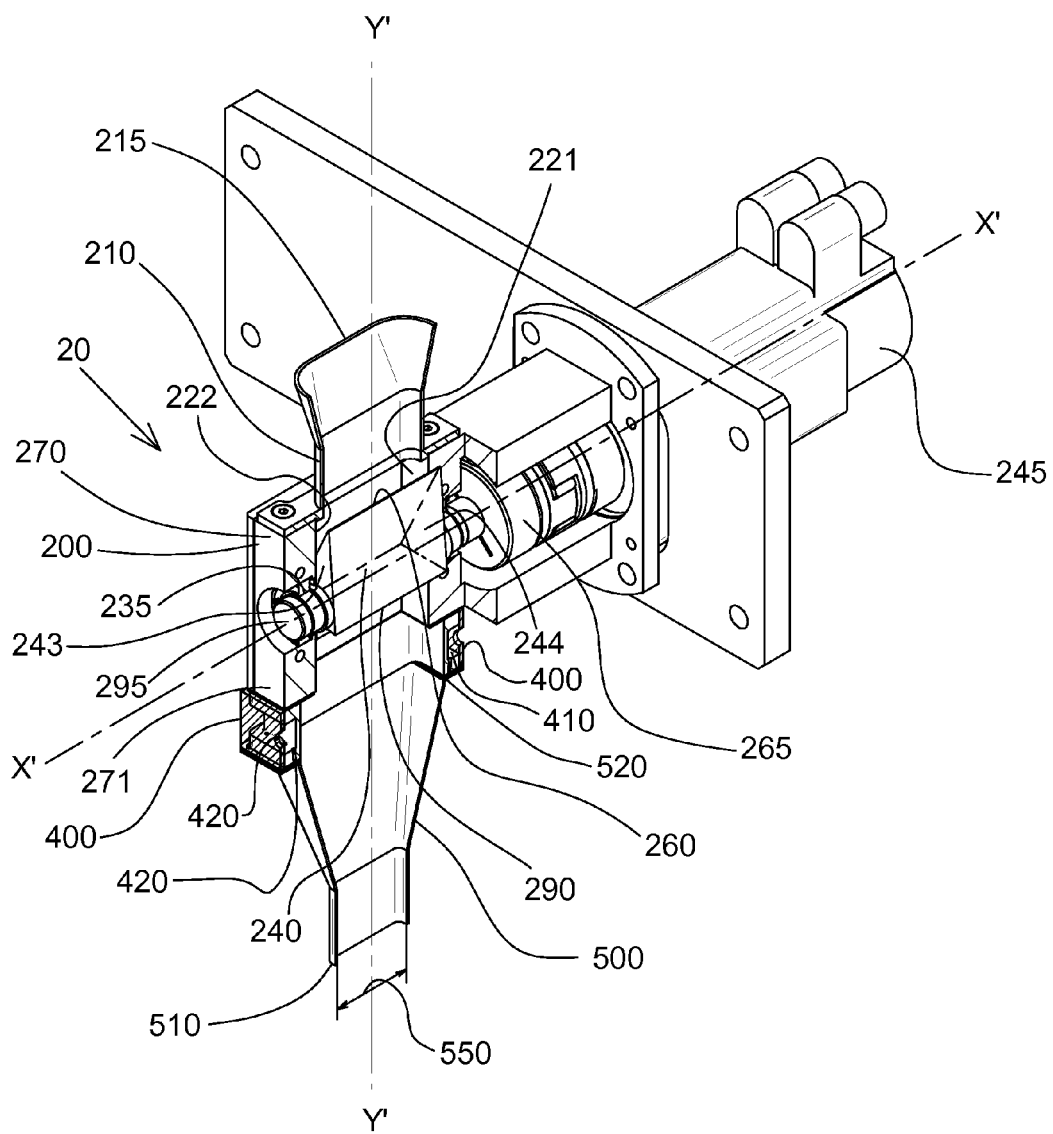
FIG. 2 is a schematic perspective view in half-view and half-section according to the axis II-II of FIG. 1 of the apparatus, subject of the present invention, according to a preferred embodiment.
Figure 6:
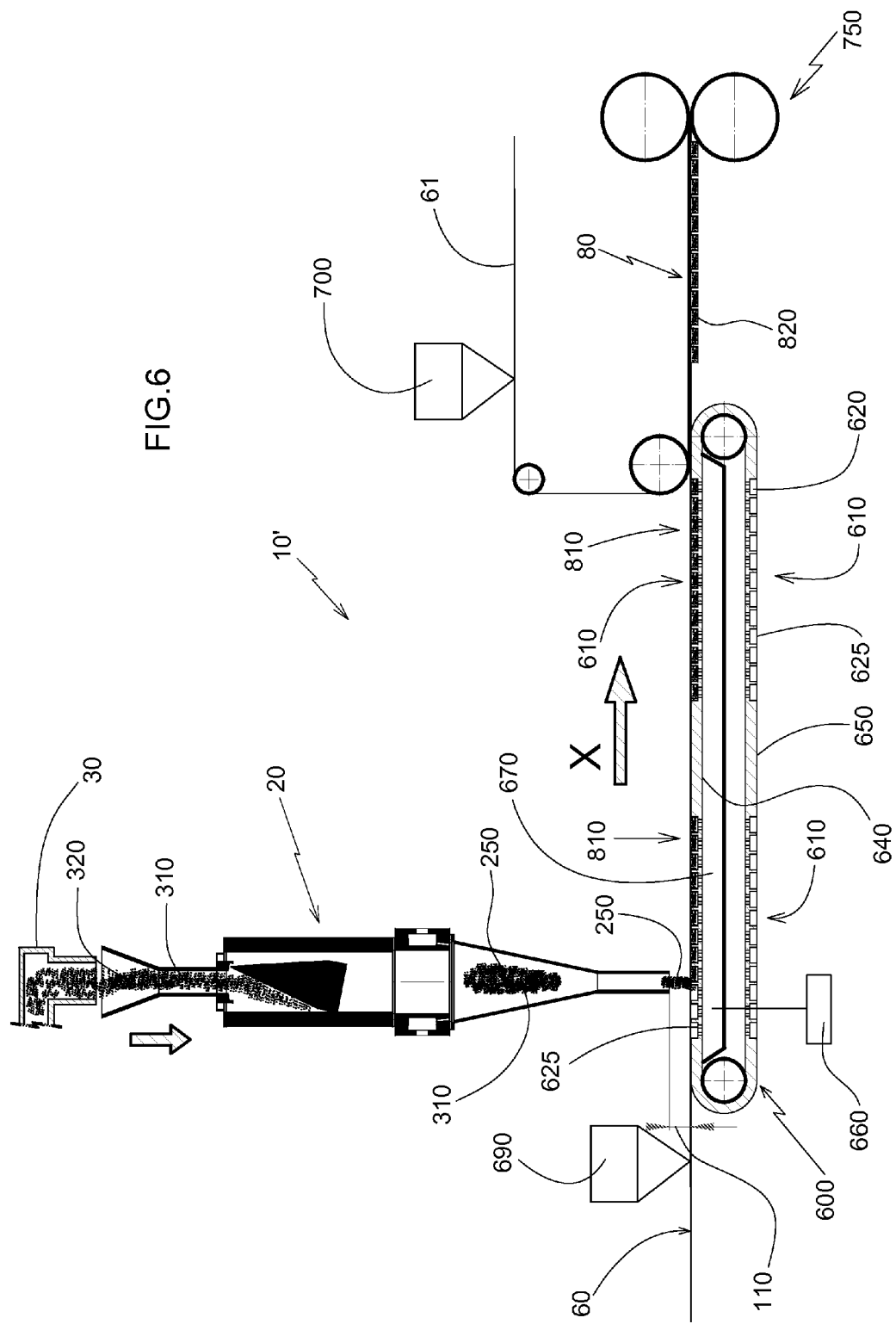
Figure 7:
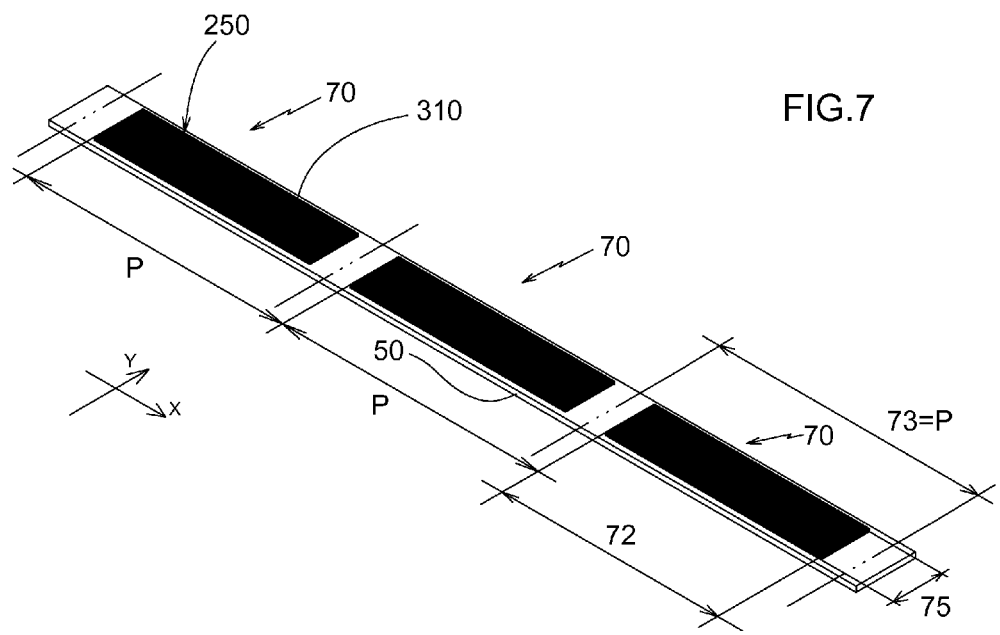
FIG. 7 is a schematic perspective view of the absorbent structure produced with the production method of FIG. 1.

The references used herein are for convenience only and therefore do not define the field of protection or the scope of the embodiments With reference to FIGS. 1 and 6, numerals 10 and 10' indicate two production methods for producing absorbent structures or parts of them, which employ a device 20, according to the preferred embodiment illustrated in FIG. 2, which makes them capable of carrying out discontinuous applications at a constant pitch P of discrete quantities of controlled weight and size 250 of absorbent polymer material in granules 310 on a continuous strip 50, 60 that moves in the advancing direction X, supported by appropriate support means, which can be either a roller or a conveyor belt 40, 600.

Said sheet 50, 60, once supplied with the absorbent material in granules 310 can be advantageously used, alone, or in combination with other materials, such as absorbent structures in disposable sanitary hygiene products. Said strip or sheet 50 or 60 can be made from synthetic and/or natural fibers that can be absorbent, such as for example cellulose fibers as shown in the production method of FIG. 1 or, alternatively, they can use a sheet of non-absorbent fibers such as, for example, a strip of non-woven fabric, as shown in the production method of FIG. 6.

The production methods 10 or 10', respectively schematized in FIG. 1 and FIG. 6, can be composed of a dispenser 30, arranged to provide a continuous flow 320 of absorbent material in granules of constantly controlled weight, to a device 20, produced according to the preferred embodiment illustrated in FIGS. 2 to 5.

A type of absorbent material in granules 310 frequently used in the manufacture of absorbent structures for disposable hygiene products, which can be advantageously managed by the device 20, according to the embodiment illustrated in FIG. 2, can be the super absorbent polymer of medium permeability Z3403 produced and marketed by Evonik Industries AG, Rellinghauser Strasse 1-11, 45128 Essen, Germany.

A continuous dispenser 30 particularly suitable for this type of production method can be the weight subtraction dispensing system model AI-405-105R-1 produced and marketed by Acrison. Inc., 20 Empire Blvd, Moonachie, N.J. 07074 U.S.A.

This type of dispenser 30 is able to provide a constant-mass flow 320 of absorbent polymer material in granules 310, independently from any variable that can influence it, such as the pressure head variation in the loading reservoir, or the variation of apparent density linked to any one of the factors that may condition it. Indeed, the dispenser 30 is normally provided with a control system of the weight, which constantly checks the weight variation according to the quantity of material 310 provided to the downstream process in the unit of time. Said control system is able to properly modulate the flow 320 in order to always maintain the mass of the material 310, supplied to the downstream process, within the predefined tolerance limits.

The sizing and selection of the continuous dispenser 30 is carried out by multiplying the number of absorbent structures that the production line must produce in the unit of time by the quantity of absorbent material in granules 310 of each dose 250 applied on each of said absorbent structures.

For example, considering that the methods and apparatus suitable for the production of the absorbent structures illustrated in FIGS. 1 and 6 can advantageously produce 700 absorbent structures per minute, with doses 250, for example, from 10 grams of absorbent material in granules 310, it follows that the continuous dispenser 30 will be able to provide a continuous and controlled flow 320 of 420 kg/hour of the said material in granules 310.

A unit or device 20 can be placed downstream of the dispensing system 30, which transforms the continuous flow 320 of polymer in granules 310 into an intermittent flow consisting of a plurality of determined and discrete quantities (or doses) 250 of said absorbent material in granules 310 and applies the said doses 250 at a constant pitch P on the relative moving substrate 50, 60.

Figure 3:
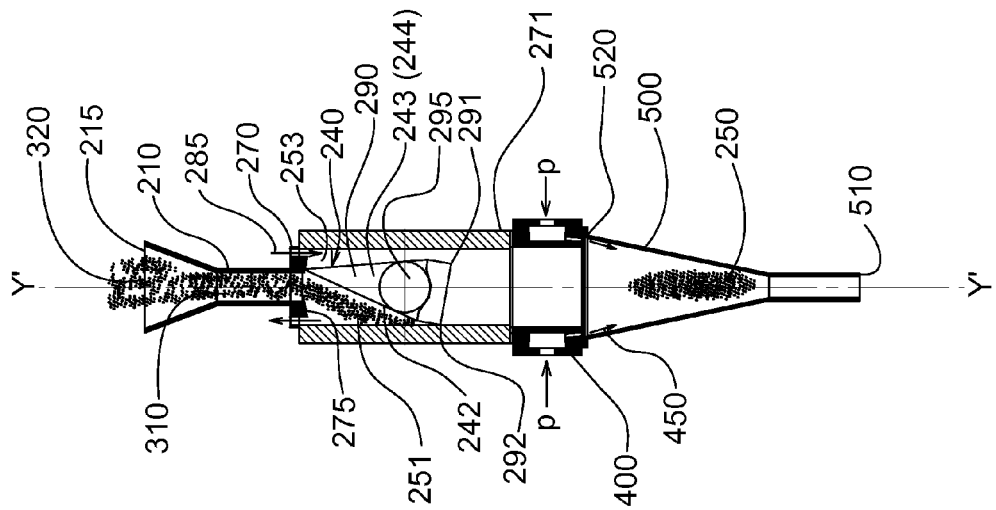
FIGS. 3 to 5 are schematic sectional views of the apparatus of FIG. 2, in the various processing steps.
Figure 4:
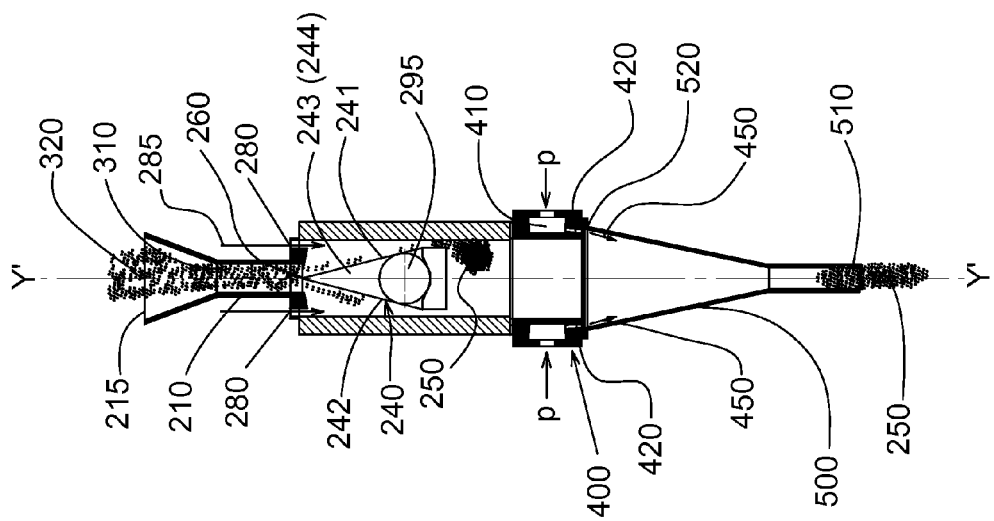
Figure 5:
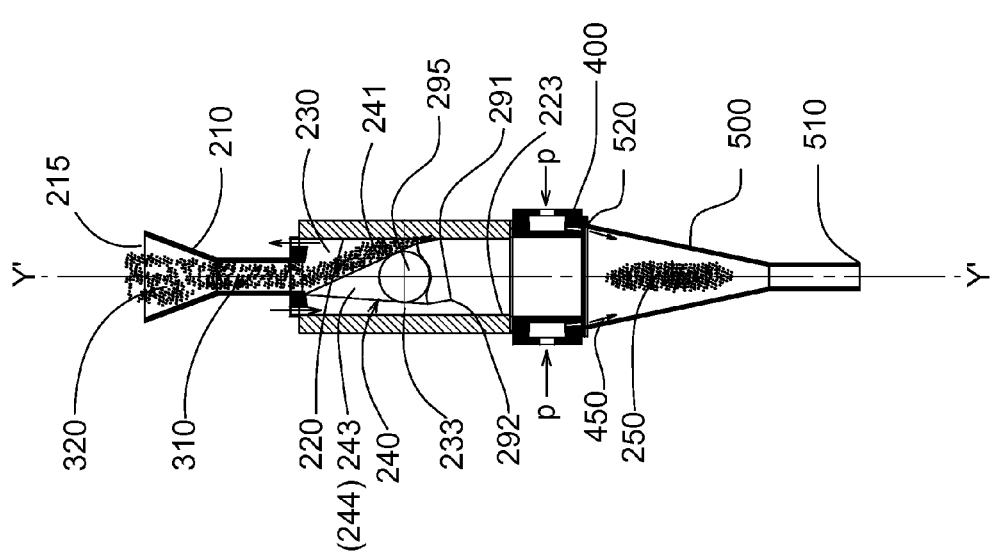

In the preferred embodiment, as illustrated in FIGS. 3 to 5, the constant-mass flow 320 of the absorbent polymer material in granules 310 is supplied to the apparatus or device 20 through the mouth 215 of the feed manifold 210 and the material then comes out in weight- and size-controlled doses 250, from the outlet nozzle 500 after having crossed the main body 200 located between said feed manifold 210 and said outlet nozzle 500. The absorbent material in granules 310, in crossing the device 20, flows along a direction Y'-Y', coincident with the respective axes of symmetry of the feed manifold 210, the outlet nozzle 500 and the main body 200, as clearly illustrated in FIG. 2. In the preferred embodiment, the main body 200 of the apparatus or device 20 has an inner section, transverse to the crossing direction Y'-Y' of said material 310, of a quadrilateral shape with all right angles.

The main body 200 has, in addition, an upper part 270 and a lower part 271.

The material in granules 310 enters inside the main body 200 of the said apparatus 20, by crossing the feed manifold 210, as is clearly highlighted in FIG. 3.

In the preferred embodiment illustrated in FIG. 2, a movable element 240 is housed within said main body 200, which can have a wedge-shape having a first and a second end 260, 290 and two side faces 241, 242, symmetrical along the crossing direction Y'-Y' of the flow of absorbent material in granules 310, converging toward the first cusp end 260.

The first cusp end 260 of the movable element 240, in the preferred embodiment of FIG. 2, is oriented upstream with respect to the crossing direction Y'-Y' of the flow of material in granules 310.

Also in the preferred embodiment of FIG. 2, the two side faces 241, 242 of the movable element 240, form with the wider second end 290, a first side edge 291 and a second side edge 292, respectively; furthermore, said movable element 240 can be connected at said second end 290 to a shaft 295, free to rotate around its axis X'-X', in order to allow the movable element 240 to make a 2θ oscillation about the said axis X'-X' between a first working position represented in FIG. 3, and a second working position illustrated in FIG. 5.

The shaft 295 is, in turn, connected to the main body 200 by means of a pair of suitable supports 235, which can be formed by bearings of any type, in the preferred embodiment of FIG. 2 they are rigid ball bearings.

The said shaft 295 is, furthermore, connected with mechanical connecting means 265 to appropriate actuator means 245.

In the preferred embodiment of FIG. 2, the said mechanical connecting means 265 can be made from components of a constant velocity joint of the type ROTEX GS28 98SH produced and marketed by KTR KUPPLUNSGSTECHNIK Gmbh, Rodder Damm 170, 48432 Germany.

Also in the preferred embodiment of FIG. 2, appropriate actuating means 245, suitable for this type of use, could be a servomotor of the type MSK 071 E-0300 and a control system HMS 54A BASIV V3 (not illustrated in the figures), produced and marketed by Bosch Rexroth AG, Electric Drives and Controls, P.O. Box 1357, 97803 Lohr, Germany.

Figure 9:
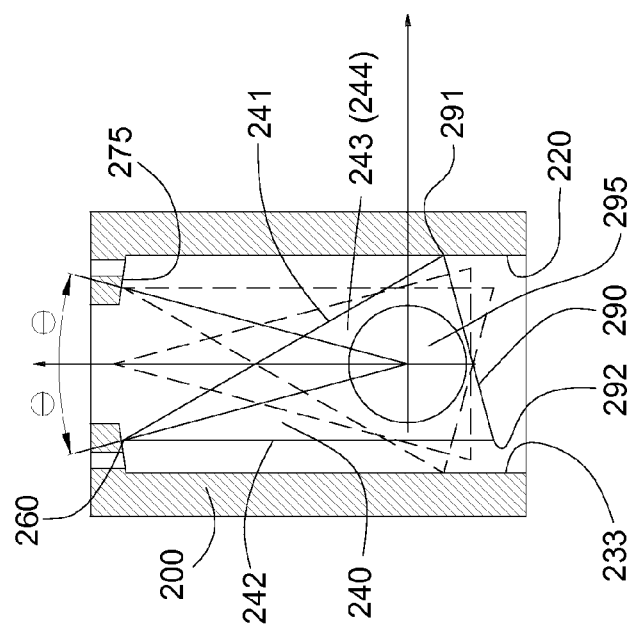
FIG. 9 is a schematic view of the movement that is carried out by the movable component of the apparatus of FIG. 2.

In the preferred embodiment, as already mentioned and clearly highlighted in FIGS. 3 to 5, the actuating means 245 are able to move the movable element 240 between a first and a second working position, causing it to oscillate through an angle 2θ that can be between 10° and 30°, with a preferred value of 20° (θ=10°), as shown schematically in FIG. 9.

An expert in the field will appreciate that the inner surface 275 of the upper end 270 of the main body 200 in the preferred embodiment is suitably shaped to allow the first end 260 of the movable element to move between the two working positions, whilst always remaining adherent to the said inner surface 275.

When said movable element 240 is located in the first working position, which in the preferred embodiment is illustrated in FIG. 3, it forms with the first inner side surface 220 and with the inner transverse walls 221 and 222 of the main body 200 of the apparatus 20, a first accumulation chamber 230, which is transversely bordered by the two said transverse walls 221 and 222 (FIG. 2) and laterally by the first inner side surface 220 and the first side face 241 of the movable element 240, so that the first side face 241 of said movable element 240 extends between the two inner transverse walls 221 and 222 of the main body 200, and connects, with its first cusp end 260 and with its first side edge 291 of the second end 290, the inner surface 274 of the upper end 270 of the main body 200 to the lower part of the first inner side surface 220 of the main body 200.

When the movable element 240 is located in the first working position, in addition to forming the first storage chamber 230, it forms a first discharge duct 233 with its second side face 242 in cooperation with the two inner transverse walls 221, 222 and with the second inner side surface 223 of the main body 200, as clearly illustrated in FIG. 3.

The apparatus 20 remains in this configuration for the time required to collect the necessary quantity of absorbent polymer material in granules 310 for the formation of a single dose 250 inside the first accumulation chamber 230.

When the loading operation of the absorbent polymer material in granules 310 in the first accumulation chamber 230 is completed, the movable element 240, thanks to the servomotor 245, is moved with a suitable velocity profile, toward the second working position, represented in FIG. 5, wherein the movable element 240 forms the second accumulation chamber 251 and the second discharge duct 253. In this second working position, the movable element 240 forms, with the second inner side surface 223 and the inner transverse walls 221 and 222 of the main body 200 of the apparatus 20, a second accumulation chamber 251 which is transversely bordered by the two said transverse walls 221 and 222, and laterally by the second inner side surface 223 and the second side face 242 of said movable element 240, so that said second side face 242 of said movable element 240 extends between the two inner transverse walls 221 and 222 of the main body 200, and connects, with its first cusp end 260 and with its second side edge 292 of the second end 290, the inner surface 274 of the upper end 270 of the main body 200 to the lower part of the second inner side surface 223 of the main body 200.

Simultaneously, the movable element 240 moving from the first to the second working position, forms a second discharge duct 253 with its first side face 241 in conjunction with the two inner transverse walls 221 and 222 and with the first inner surface 220 of the main body 200, from which the absorbent material in granules 310 flows of the dose 250 previously collected in the first accumulation chamber 230.

In the preferred embodiment 20, illustrated in FIG. 2, the first and the second accumulation chambers 230, 251 formed by the movement between the first and second working positions of the movable element 240 with the inner surfaces 220, 221, 222, 223 of the main body 200 are characterized in that they ensure the sealing of the absorbent material in granules 310. Said sealing can be effectively obtained by appropriate coupling tolerances between the surfaces 241, 242, 243, 244 of the movable element 240 and the inner surfaces 220, 221, 222, 223 of the main body 200. In the preferred embodiment 20, it is possible to obtain a distance from 0.05 to 0.2 mm between the two connecting surfaces 243, 244 between the first and second side faces 241, 242 of the movable element 240 and the respective inner transverse walls 221, 222. Similarly, the same distance can be obtained between the first cusp end 260 of the movable element 240 and the inner surface 274 of the upper end 270 of the main body 200. Also in the preferred embodiment 20 of FIG. 2, however, the first and second side edges 291, 292 of the second end 290 of the movable element 240 can come in contact with the respective first and second inner surfaces 220, 223 of the main body 200.

Figure 10:
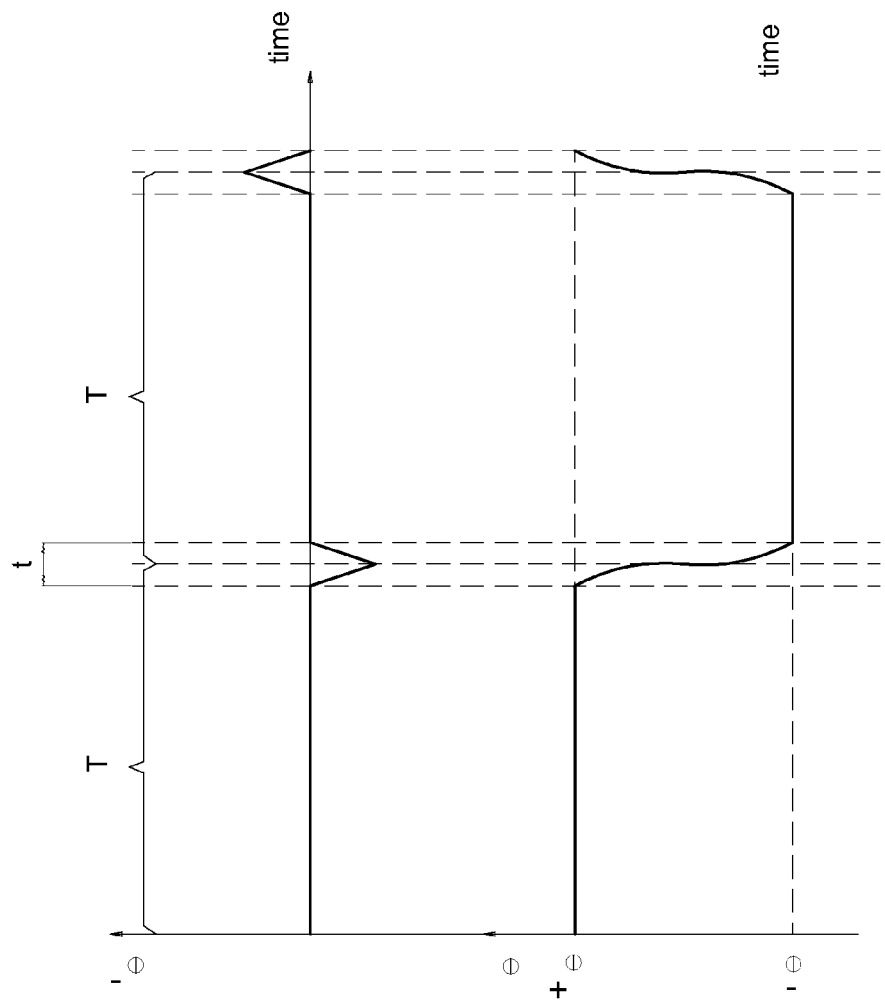
FIG. 10 is a diagram of the law of motion of the component of FIG. 9.

In the preferred embodiment, the movable element 240 is moved between the two working positions, clearly highlighted in FIGS. 3 and 5, with a velocity profile that is represented in the upper part of the graph of FIG. 10, from which it can be appreciated, by way of example, that in view of a cycle time T=0.00857 seconds, necessary for the production of an absorbent structure 310 in a production line that produces 700 articles per minute, the time t that it takes for the movable element 240 to move between the said two working positions can be between 15% and 40% of the cycle time, with a preferred value of 25%, which in this specific case would be t=0.00214 seconds.

The skilled person will appreciate that said velocity profile, in combination with the constant control of both the mass of the material in granules 310 of the flow 320 carried out by the dispenser 30, and the time of exposure to the said flow 320 of the relative accumulation chamber 230, 251, allows the device 20, in the preferred embodiment illustrated in FIG. 2, to produce a multiplicity of doses 250, all having the same quantity, in terms of weight, of absorbent material in granules 310.

FIG. 4 clearly shows how the fast movement of the movable element 240 between the two working positions minimizes the risk that there could be a contamination of granules of absorbent material 310 in those areas of the sheet 50, 60 which should remain devoid of granules, indeed, the speed of the movement minimizes the quantity of material that might accidentally fall into the discharge duct before it is closed in the respective accumulation chamber, as clearly shown in FIG. 5.

FIG. 4 also clearly illustrates, in the preferred embodiment, the discharge operation of the material in granules 310 is favored by the presence of air inlets 280 located on the upper part 270 of the main body 200.

Indeed, these air inlets 280, which in the preferred embodiment can be slots or holes, allow the air flow 285 to fill the void that is generated in the respective discharge ducts 233, 253 when the granular material 310 flows toward the output nozzle 500, which, in turn, serves to convey it onto the moving sheet 50, 60.

The skilled person will appreciate the fact that the said openings 280 also favor the loading step of the material 310, facilitating the evacuation of the air present in the respective accumulation chambers 230, 251, as shown schematically in FIGS. 3 and 5.

While the apparatus 20 carries out the said operations, the dispenser 30 delivers a continuous, constant-mass flow 320 of absorbent polymer material in granules 310 to the mouth 215 of the feed manifold 210, filling, as such, alternately, the two accumulation chambers 230, 251, which, subsequently, will be emptied when they transform into the respective discharge ducts 233, 253.

The cyclic repetition of the operations just described allows the transformation of the continuous, constant-mass flow 320 of the absorbent polymer material in granules 310 into an intermittent flow consisting of a plurality of discrete determined quantities or doses 250 of absorbent material in granules 310 that can be deposited on a substrate or sheet 50, 60 that, in the production methods of FIGS. 1 and 6 that use the device 20 according to the preferred embodiment of FIG. 2, for example, can move along the working direction X at a linear velocity of 4.667 m/s, which is, in fact, the velocity required to produce 700 absorbent structures per minute, each having a length of 400 mm.

It will not escape the skilled person that the left to right motion of the X direction used in the figures attached to the present description is only used for indicative purposes, since the apparatus of the present invention can work equally well in the opposite direction, i.e. from right to left.

In the preferred embodiment of the device 20, as clearly represented in FIGS. 1 to 6, the output nozzle 500 can be connected to the lower part 271 of the main body 200 by means of a manifold 400 interposed between said two elements 500, 200.

The manifold 400, in the preferred embodiment of FIG. 2, is provided with a reservoir for pressurized air 410, which surrounds the outer perimeter of the manifold 400 itself, and that serves to supply the openings 420 located at the connecting edge 520 of the nozzle 500 with the manifold 400, and is able to generate a high speed air flow 450 within said output nozzle 500. The velocity of the airflow 450 may vary from 100 to 300 m/s.

In the preferred embodiment, this characteristic is achieved with holes 420, created on the four sides of the manifold 400, having a diameter between 1 and 2.5 mm and placed at a distance between 5 and 15 mm; in a further preferred configuration, said holes may have a diameter of 1.5 mm at a distance of 10 mm.

The air flow 450 performs two fundamental functions: the first is to generate a sub-atmospheric pressure level at the entrance of the outlet nozzle 500 thanks to the Venturi effect, generated by the high speed air, which, in cooperation with the airflow 285 flowing through the air inlets or openings 280, is able to extract the dose 250 of the material in granules 310 accumulated within the respective accumulation chambers 230 and 251 with greater energy, as clearly illustrated in FIG. 4; the second function is to perform a lamination of each individual dose 250. Indeed, when the movable element 240 moves between the two working positions, and opens the relative discharge duct 233, 253, the material in granules 310 of the single dose 250, previously contained in the corresponding accumulation chamber 230, 251, is extracted in a block, also by virtue of the pressure gradient generated by the Venturi effect of the air flow 450. As soon as the granules 310 of the dose 250 are captured by the airflow 450, they are accelerated to a higher speed with respect to that possessed by the entire dose 250 in the initial discharge step, with the consequence of carrying out a stretching or lamination of the dose 250 itself. Thanks to this effect, or rather, thanks to the adjustment of the airflow 450 velocity, the length 72, 82 of the single dose 250 can be controlled and varied, if necessary.

In the preferred embodiment, the airflow 450 velocity can be varied by suitably adjusting the value of the air pressure inside the reservoir 410. Adequate air pressure values are between 0.3 and 4 bars, particularly preferred are values between 0.7 and 1.5 bars.

A simple and effective system to adjust said pressure level is to connect the reservoir 410 to the apparatus that generates pressured air, interposing between them a pressure-adjusting device of the type R73G-3GK-NMR, produced and marketed by Norgren SpA, via Trieste 16, 20871 Vimercate (MB).

The outlet nozzle 500, in the preferred embodiment, as well as performing the functions of conveying the dose 250 of absorbent granular material 310 toward the moving sheet 50, 60, and defining and controlling the length 72, 82, also performs the function of controlling the width 75, 85 of each single dose 250 of granular material 310 applied on the said sheet 50, 60, so that the width 75, 85 of the said doses 250 is determined precisely by the width 550 of the end portion of the outlet nozzle 500.

In a further preferred configuration, not shown in the attached figures, in order to ensure a better control of said width 75, 85 of the doses 250, the main elements of the apparatus 200, or rather, the feed manifold 210, the movable element 240, the main body 200, the compressed air manifold 400 and the outlet nozzle 500, are produced so that they all have an inner duct width for the passage of absorbent material in granules 310 equal to the width 75, 85 required for the single dose 250. Indeed, in this further configuration, there are no variations in the width of the inner passages of the absorbent material in granules 310 which, therefore, is not subject to transverse direction changes; this ensures, therefore, a more constant and regular flow of the material in granules 310 and, ultimately, a better control of the width 75, 85 of doses 250.

The skilled person will appreciate that the device 20, in the preferred embodiment illustrated in FIG. 2, could be made from stainless steel AISI 304, in particular those components that are in direct contact with the absorbent material in granules 310. Indeed, the latter, being highly hygroscopic, can trigger possible corrosion processes if it comes in contact with non-corrosion-resistant metallurgy, and possible surface treatments would not provide protection because they would be removed in a short time by the abrasive action of the material 310 itself.

The skilled person will appreciate, furthermore, that the outlet end 510 of the nozzle 500 from which the absorbent granular material 310 flows out may be placed at a distance 110 from the respective moving strip 50, 60, which can vary, from a minimum value of 0.1 millimeters to a maximum value of 40 millimeters. It is clear that this variability depends on several factors, such as the size of the granules of the material, the quantity of material 310 required for each dose 250, as well as process parameters such as the type and nature of the strip 50, 60 to which said absorbent material into granules 310 is applied.

In the production method 10 illustrated in FIG. 1, the apparatus 20 of discontinuous application of controlled quantities 250 of absorbent polymer material in granules 310, according to the preferred embodiment of FIG. 2, can be used in combination with a continuous strip 50 made of a layer of absorbent cellulose fibers, and the said application method of the doses 250 can be carried out either when said layer 50 of cellulose fibers is already formed, as shown in FIG. 1, or during the formation of the layer 50 itself.

In this type of production method of the absorbent structure 70, the distance 110 between the outlet end 510 of the nozzle 500 and the sheet 50 can be in the range from a minimum of 15 to a maximum of 40 millimeters, with a preferred value of 30 millimeters, this is to favor a more thorough mixing of the granules 310 with the constituent fibers of the support layer 50, especially in the case where the absorbent polymer granules 310 are applied during the construction step of the said layer 50.

In the production method example 10' illustrated in FIG. 6, the apparatus 20 of the discontinuous application of controlled quantities 250 of absorbent polymer material in granules 310, according to the preferred embodiment of FIG. 2, can be used to produce the absorbent structure 80 that is produced by filling the hollow- or small well-formations 820 with absorbent material in granules 310 present on a sheet 60, typically made of a Non-Woven material strip. The hollow- or small well-formations 820 of each absorbent structure 80 can be present in array-form 810 of parallel rows 850 of cells or hollows or wells 820.

Figure 8:
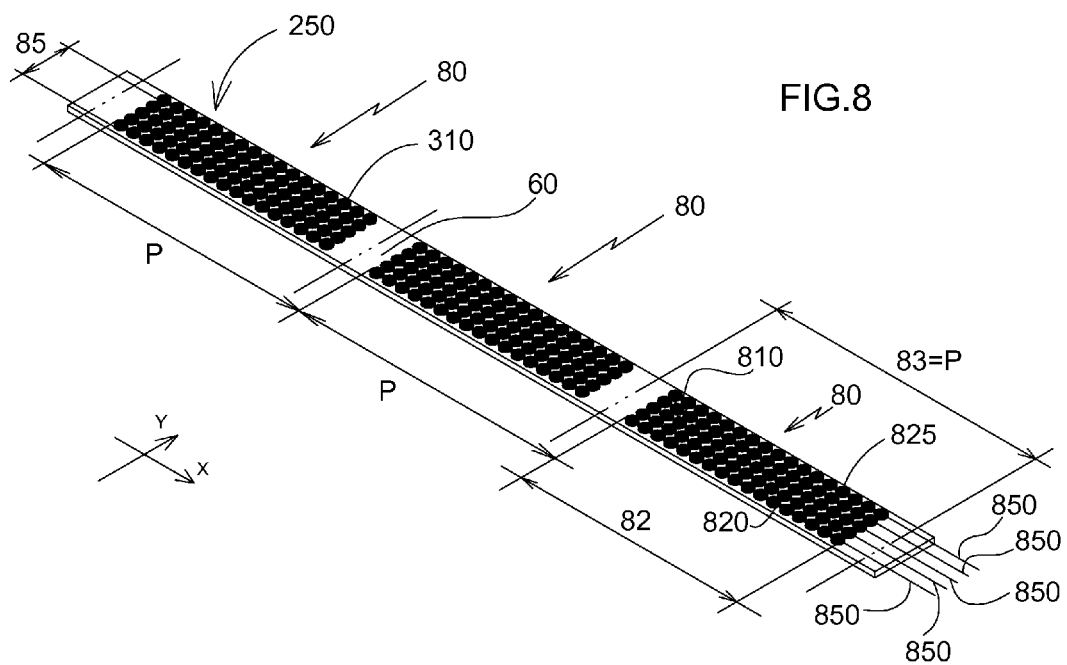
FIG. 8 is a schematic perspective view of the absorbent structure made with the production method of FIG. 6.

Each of the said cells or hollows 820 has a mouth profile 825, which may be circular, as shown in FIG. 8, or hexagonal, or any other shape.

A suitable sheet for producing the absorbent structure 80 is the 10 g/m$^2$ hydrophilic SMS, code IC3EW-100 010 DB W, produced and marketed by Fitesa 840 SE Main Street, Simpsonville, S.C. 29681 U.S.A.

For producing the absorbent structure 80 briefly described above, the support sheet 60 is conveyed on a support apparatus, which may be either a drum or, as illustrated in FIG. 6, a belt 600, provided on its outer surface 650 with a plurality of groupings 610 of recesses 620 with the profile that reproduces the desired shape of the cavities or wells 820. The arrays 810 are spaced at a constant pitch P that is equivalent to the length 83 of the absorbent structure 80. The support sheet 60 is deposited on the forming belt 600, and subjected to deformation, for example by the action of a possible pressure roller (not present in the method illustrated in FIG. 6), provided on its outer surface with a plurality of protrusions corresponding to the shape and position of the recesses 610 on the outer surface 650 of the belt or drum 600, in combination with the action of a sub-atmospheric pressure source 660 applied on the inner surface 640 of the belt or drum 600 through a vacuum distributor 670. The vacuum generated by the sub-atmospheric source 660, thanks to the presence of air permeable surfaces 625 on the bottom of the cavities 620, when these air permeable surfaces are alongside the vacuum distributor 670, sucks the sheet 60 inside the said cavities 620 of the forming belt 600, determining the deformation with the consequent formation of the cavities or wells 820.

It will not escape the skilled person that the said deformation operation can also be carried out by just one of the two devices described above, indeed, as highlighted in the diagram of FIG. 6, the deformation of the sheet 60 is achieved only by the vacuum action.

The forming process just described is essentially similar to the techniques of vacuum deformation of plastic material films, and can be advantageously implemented either on belt systems or on drum apparatus, as for example described in the documents EP 1 974 705 A1 and EP 2 286 776 A1.

In the production method example 10', illustrated in FIG. 6, the apparatus 20 will deposit the dose 250 of absorbent polymer material in granules 310 within the cavity 820 of the relative array 810 previously formed on the strip 60. In this particular process, the distance 110 between the outlet end 510 of the nozzle 500 and the sheet 50 can be within a range from a minimum of 0.1 to a maximum of 5 mm, with a preferred range between 0.5 and 1 mm, so as to avoid any rebounds of the absorbent material in granules 310 on the sheet 60 supported by the belt 600, and therefore avoiding contamination in areas where the material in granules should not be present.

In the method 10', the deposition step of the dose 250 of the absorbent material in granules 310 coincides with the construction step of the array 810 of cavities 820; therefore, the device 20 will begin to deposit the material in granules 310 of the dose 250 in the instant in which the first cavities or hollows 820 present themselves under the mouth or outlet end 510 of the nozzle 500, and the unloading operation will cease when all the cavities 820 of the relative array 810 have passed under said mouth or outlet end 510 and therefore will have been filled with absorbent material in granules 310.

In a further particularly preferred embodiment of the device 20, the outlet nozzle 500 can be subdivided into a plurality of ducts separated from each other along the respective width 550 and arranged alongside one another, designed to carry out an application of material in granules that results as being discontinuous in the Y direction, transverse to the direction of application/advancement X and to the said sheet 50, 60.

It is evident to the skilled person that said further embodiment can be advantageously applied in the production method 10' illustrated in FIG. 6, i.e. in the case wherein the apparatus 20 must fill, with single doses 250 of absorbent material in granules 310, the corresponding arrays 810 formed, in turn, by a plurality of rows 850 of wells or cavities 820 parallel to each other; in this case an outlet nozzle 500 can be used, provided with a series of ducts arranged next to one another, wherein each outlet duct is coaxial with the respective row 850.

The absorbent structure 80 can be completed by sealing the absorbent material in granules 310 within the hollows 820 with a further sheet of Non-Woven material, and providing appropriate means for closing and anchoring the absorbent material in granules 310 such as, for example, mechanical systems 750 or glue-application systems 690, 700.

Of course, without prejudice to the principle of the invention, the details of construction and the embodiments may vary widely with respect to those described and illustrated without departing from the scope of the invention as defined by the claims that follow.

The invention claimed is:

1. A method for intermittently applying a flow of granular material on a sheet, comprising:
   advancing a continuous sheet;
   providing a continuous and weight-controlled flow of granular material;
   providing a main body having an inlet mouth, an outlet nozzle, a hollow chamber between the inlet mouth and the outlet nozzle, and a movable element housed in said hollow chamber which oscillates between a first and a second working position, the movable element in said first and second working positions forming in said hollow chamber a first accumulation chamber and a first discharge duct, and a second accumulation chamber and a second discharge duct, respectively;
   alternately moving said movable element between said first and second working positions while feeding said continuous and weight-controlled flow of granular material to said inlet mouth of said main body, so as to alternately fill said first and second accumulation chambers;
   alternately expelling the granular material contained in said first and second accumulation chambers through said first and second discharge ducts; and
   applying said granular material discharged through said first and second discharge ducts to said advancing continuous sheet.

2. A method according to claim 1, wherein said granular material contained in said first and second accumulation chambers is expelled with pneumatic extraction means.

3. A method according to claim 2, wherein said pneumatic extraction means exploits the Venturi effect.

* * * * *